| United States Patent [19] | [11] Patent Number: 4,800,196 |
| Nomura et al. | [45] Date of Patent: Jan. 24, 1989 |

[54] PHENYL SALICYLATE AND BENZYL SALICYLATE AS ACARICIDAL AGENTS

[75] Inventors: Yoshiharu Nomura; Shigemasa Aoki; Akira Nishimura, all of Ako, Japan

[73] Assignee: Earth Chemical Co., Ltd., Hyogo, Japan

[21] Appl. No.: 41,071

[22] PCT Filed: Dec. 6, 1985

[86] PCT No.: PCT/JP85/00675

§ 371 Date: Mar. 27, 1987

§ 102(e) Date: Mar. 27, 1987

[87] PCT Pub. No.: WO87/00728

PCT Pub. Date: Feb. 12, 1987

[30] Foreign Application Priority Data

Aug. 6, 1985 [JP] Japan ................... 60-173867
Aug. 6, 1985 [JP] Japan ................... 60-173868

[51] Int. Cl.$^4$ ............................................. A01N 37/36
[52] U.S. Cl. .................................................. 514/159
[58] Field of Search ....................................... 514/159

[56] References Cited

U.S. PATENT DOCUMENTS

| 1,953,629 | 4/1934 | Pfaff et al. | 514/159 |
| 1,963,955 | 6/1934 | Cleveland | 514/159 |
| 1,974,689 | 9/1934 | Pfaff et al. | 514/159 |
| 2,480,084 | 8/1949 | Mayer | 514/159 |
| 3,091,511 | 5/1963 | Calhoun | 514/159 |
| 4,666,940 | 5/1987 | Bischoff et al. | |

FOREIGN PATENT DOCUMENTS

| 0147947 | 7/1985 | European Pat. Off. | |
| 0173229 | 3/1986 | European Pat. Off. | |
| 61-87603 | 5/1986 | Japan | 514/159 |
| 60142906 | 7/1988 | Japan | |
| 60163805 | 8/1988 | Japan | |
| 1246305 | 9/1971 | United Kingdom | |
| 2042893 | 10/1980 | United Kingdom | |

OTHER PUBLICATIONS

English Translation of Japanese Pat. No. 45-38354, 12/4/70; 4 pages.
Chemical Patents Index, Basic Abstracts Journal, Section C, Week 24, 1986, Ref. No. 153387.
Chemical Abstracts, vol. 86, No. 13, Ref. No. 84706W.
Patent Journal, Wed. 20 Sep. 1967; 2A, A 67/2464.
Chemical Abstracts, vol. 90, No. 22, Abstr. No. 174071x.
Chemical Abstracts, vol. 73, No. 13, Abstr. No. 65437z.

*Primary Examiner*—Allen J. Robinson
*Attorney, Agent, or Firm*—Armstrong, Nikaido, Marmelstein & Kubovcik

[57] ABSTRACT

Acaricides characterized by containing at least one member selected from phenyl salicylate, diphenylamine, methyl β-naphtyl ketone, coumarin, phenethyl benzoate, benzyl salicylate, N-fluorodichloromethyl-thio-cyclohexene-dicarboxyimide, p-nitrobenzoic acid methyl ester, p-chlorometaxylenol, α-bromocinnamic aldehyde, 2,5-dichloro-4-bromophenol, N,N-dimethyl-N'-tryl-N'-(fluorodichloromethylthio)-sulfamide, 2-phenyl-phenol, sodium 2-phenyl-phenolate, 5-chloro-2-methyl-4-isothiazoline-3-one, 2-methyl-4-isothiazoline-3-one and benzimidazolyl methyl-carbamate as an active ingredient.

4 Claims, No Drawings

PHENYL SALICYLATE AND BENZYL SALICYLATE AS ACARICIDAL AGENTS

TECHNICAL FIELD

The present invention relates to new acaricides and mite proof materials.

BACKGROUND ART

There are certainly some kinds of mites in a house dust of general houses and in recent years, frequent breeding of mites has been observed according to change of houses and life style. Hitherto, there have been known some kinds of acaricides for mites in a house dust, for example, phosphorated compounds such as phenitrothione, phenthione, DDVP and diazinon, carbamated compounds such as propoxer and NAC and the pyrethroided compounds such as dl,d-T80-resmethrin.

These known acaricides, which are used by being supported in a tatami, a carpet or an insect control paper or scattered or sprayed as they are, have such problems as the following: the acaricides of phosphorated compounds have high toxicity, bad smell and low effect on Epidermoptidae, those of carbamated compounds also have high toxicity and low effect on Epidermoptidae, those of pyrethroided compounds are expensive and have low effect on *Tyrophagus putrescentiae*, and it is difficult to use the above acaricides in combination with one another.

DISCLOSURE OF THE INVENTION

As a result of various studies for providing an inexpensive acaricide having low toxicity and wide range of prevention of mites in a house dust, the following compounds are found to satisfy the above conditions: phenyl salicylate, diphenylamine, methyl β-naphthyl ketone, coumarin, phenetyl benzoate, benzyl salicylate, N-fluorodichloromethyl-thio-cyclohexene-dicarboxyimide, p-nitrobenzoic acid methyl ester, p-chlorometaxylenol, α-bromocinnamic aldehyde, 2,5-dichloro-4-bromophenol, N,N-dimethyl-N'-tryl-N'-(fluorodichloromethylthio)-sulfamide, 2-phenyl-phenol, sodium 2-phenyl-phenolate, 5-chloro-2-methyl-4-isothiazoline-3-one, 2-methyl-4-isothioazoline-3-one and benzimidazolyl methyl-carbamate.

Thus, the present invention relates to acaricides characterized by containing at least one member selected from N-fluorodichloromethyl-thio-cyclohexene-dicarboximide, p-nitrobenzoic acid methyl ester, p-chlorometaxylenol, α-bromocinnamic aldehyde, phenyl salicylate, phenyl benzoate, diphenylamine, methyl β-naphthyl ketone, coumarin, phenethyl benzoate, benzyl salicylate, 2,5-dichloro-4-bromophenol, N,N-dimethyl-N'-tryl-N'-(fluorodichloromethylthio)-sulfamide, 2-phenylphenol, sodium 2-phenyl-phenolate, 5-chloro-2-methyl-4-isothiazoline-3-one, 2-methyl-4-isothiazoline-3-one and benzimidazolyl methyl-carbamate as an active ingredient and mite proof materials characterized by supporting these acaricides in substrates.

BEST MODE FOR CARRYING OUT THE INVENTION

The acaricides of the present invention have superior effects on prevention of mites by containing at least one member selected from N-fluorodichloromethylthio-cyclohexene-dicarboximide (NFC), p-nitrobenzoic acid methyl ester (NBA), p-chlorometaxylenol (PCMX), α-bromocinnamic aldehyde (BCA), phenyl salicylate (PS), phenyl benzoate (PB'), diphenylamine (DA), methyl β-naphthyl ketone (MNK), coumarin (CM), benzyl salicylate (BS), phenetyl benzoate (PB), 2,5-dichloro-4-bromophenol (CBP), N,N-dimethyl-N'-tryl-N'-(fluorodichloromethylthio)-sulfamide (TFS), 2-phenyl-phenol (OPP), sodium 2-phenyl-phenolate (SPP), 5-chloro-2-methyl-4-isothiazoline-3-one (CIO), 2-methyl-4-isothiazoline-3-one (MIO) and benzimidazolyl methyl-carbamate (BIC).

The acaricides can be applicable to any kind of mites existing in a house. Further, particular examples of the mites to which the acaricides are applicable are Epidermoptidae such as *Dermatophagoides farinae* and *Dermatophagoides pteronyssinus*, Acaridae such as *Tryophagus putrescentiae* and *Aleuroglyphus ovatus*, Glycyphagidae such as *Glycyphagus privatus* and *Glycyphagus domesticus*, Tarsonemidae, Cheyletidae such as *Cheyletus malaccensis* and *Cheyletus fortis* and animal paracitic mites such as *Ornithonyssus bacoti* and *Ornithonyssus sylviarum*.

When the acaricides of the present invention are employed, the compositions containing the above-mentioned active ingredients can be used as they are. Usually, they are used in the form of solution, emulsion, wettable powder, spray, aerosol, fumigant, paint, dust, granule or the like by supporting the compositions containing the active ingredients in a liquid or solid type support, and if necessary, by adding thereto film-coating agent, emulsifying agent, dispersion agent, spreader, moistening agent, stabilizer, propellant, volatile-controlling agent and the like.

Examples of the above-mentioned liquid type support are, water, alcohols such as methyl alcohol, ethyl alcohol and isopropyl alcohol, ketones such as acetone, methyl ethyl ketone and cyclohexanone, ethers such as tetrahydrofurane, dioxane and dimethyl ether, aliphatic hydrocarbons such as hexane, kerosine, normal paraffin and solvent naphtha, aromatic hydrocarbons such as benzene and toluene, halogenated hydrocarbons such as dichloromethane and dichloroethane, esters such as ethyl acetate and butyl acetate, and the like. Examples of the above-mentioned solid type support are mineral powders such as silicic acid, kaolin, active carbon, bentonite, diatomaceous earth, talc, clay, calcium carbonate and ceramic powder, vegetable powders such as wood powder, soybean powder, flour and starch and inclusion compounds such as cyclodextrin.

Examples of the above-mentioned film-coating agent are cellulose derivatives, vinyl resin, alkyd resin, urea resin, epoxy resin, polyester resin, urethane resin, silicone resin, acrylic resin, gum chloride, polyvinyl alcohol and the like. Examples of the above-mentioned emulsion, dispersion and spreader are soaps and surface active agents such as polyoxyethylene aliphatic alcohol ether, polyoxyethylene alkylallyl ether, polyoxyethylene fatty acid ester, fatty acid glyceride, sorbitan fatty acid ester, ester sulfate of higher alcohol and alkylarylsulfonate. Further, examples of the above-mentioned propellant are liquefied petroleum gas, dimethyl ether, fluorocarbon and the like. Examples of the volatile-controlling agents are sublimate support such as tricyclodecane, cyclododecane, 2,4,6-triisopropyl-1,3,5-trioxan and trimethylenenorbornane, sublimate insecticide such as p-dichlorobenzene, naphthaline and camphor. The above-mentioned acaricides may be used as a sublimate solid acaricide in combination with the above sublimate support or sublimate insecticide and also may be used as a volatile acaricide in combination with volatile insecticide such as empethrin and DDVP.

Furthermore, it is possible to combine various kinds of insecticide, synergist, harmful insect repellent, mouse repellent, antioxidant, antidecomposition, bactericide, fungicide, perfume, colaring agent and the like with the acaricides of the present invention. Every kind of insecticides which has been employed to exterminate vermin can be combined with these acaricides. The typical examples are 3-allyl-2-methylcyclopenta-2-ene-4-one-1-yl dl-cis/trans-chrysanthemate, 3-allyl-2-methycyclopenta-2-ene-4-one-1-yl d-cis/trans-chrysanthemate, d-3-allyl-2-methylcyclopenta-2-ene-4-one-1-yl d-trans-chrysanthemate, 3-allyl-2-methylcyclopenta-2-ene-4-one-1-yl d-trans-chrysantemate, N-(3,4,5,6-tetrahydrophthalimide)-methyl dl-cis/trans-chrysanthemate, (5-benzyl-3-furyl)methyl d-cis/trnas-chrysanthemate (hereinafter referred to as "AA"), [5-(2-propargyl)-3-furyl]methyl chrysanthemate, 3-phenoxybenzyl, 2,2-dimethyl-3-(2',2'-dichlorovinyl)cyclopropanecarboxylate, 3-phenoxybenzyl d-cis/trans-chrysanthemate, α-cyanophenoxybenzyl isopropyl-4-chlorophenyl acetate, d-3-allyl-2-methylcyclopenta-2-ene-4-one-1-yl d-trans-chrysanthemate, (S)-α-cyano-3-phenoxybenzyl (IR.-cis)-3-(2,2-dichlorovinyl)-2,2-dimethylcyclopropanecarboxylate, (R,S)-α-cyano-3-phenoxybenzyl (1R.1S)-cis/trans-3-(2,2-dichlorovinyl)-2,2-dimethylcyclopropanecarboxylate, α-cyano-3-phenoxybenzyl d-cis/trans-chrysanthemate, 1-ethynyl-2-methyl-2-pentenyl cis/trans-chrysanthemate, 1-ethynyl-2-methyl-2-pentenyl 2,2-dimethyl-3-(2-methyl-1-propenyl)cyclopropane-1-carboxylate, 1-ethynyl-2-methyl-2-pentenyl 2,2,3,3-tetramethylcyclopropanecarboxylate, 1-ethynyl-2-methyl-2-pentenyl 2,2-dimethyl-3-(2,2-dichlorovinyl)cyclopropane-1-carboxylate, O,O-dimethyl O-(2,2-dichlorovinyl)phosphate, O-isopropoxyphenyl methyl carbamate, O,O-dimethyl O-(3-methyl-4-nitrophenyl)thionophosphate, O,O-diethyl O-2-isopropyl-4-methylpyrimidyl-(6)-thiosphophate (hereinafter referred to as "AB"), O,O-dimethyl S-(1,2-dicarboethoxyethyl)dithiophosphate, isobornyl thiocyanate (hereinafter referred to as "AC") and the like.

The amount of the active ingredients in the acaricides of the present invention may be optionally determined according to its dossage form, its applying manner and place and the like. In case of using the acaricides in the form of wettable powder or emulsion, the preferable concentration of the compositions having active ingredients is from 0.1 to 50% by weight. In case of using acaricides in the form of oil or aerosol, the preferable concentration of the compositions having active ingredients is from 0.1 to 30% by weight. The preferable amount of the compositions having active ingredients to the area or the space to be treated is more than about 20 mg per 1 $m^2$ or more than about 2 mg per 1 $m^3$ respectively.

The present invention also provides mite proof materials which support the above-mentioned acaricides in substrates. The mite proof materials are used as films, sheets, building materials and the like having the property of prevention of mites according to the characteristics of the substrates. Examples of the substrates are synthetic resin sheets such as polyethylene, polypropylene, nylon, polyvinyl chloride, polyvinylidene chloride, polyester, the sheets made of animal, vegetable or inorganic fiber (papers, fabrics, non-woven fabrics, leathers and the like), sheets or blended fabrics made of these synthetic resin and inorganic fiber or powder, blended or non-woven fabrics made of the above synthetic resin and animal or vegetable fiber, metal foils or films such as alminum, stainless, zinc and the laminated sheets consisting of some of the above-mentioned sheets. Other examples are natural wood for building materials such as paulownia, pencil cedar, comphor tree and the like and plastics, for instance, moldings of vinyl chloride resin, chlorinated polyethylene, polyethylene, polypropylene and the like. There is no particular limitation of supporting means of the acaricides of the present invention in these substrates and it is possible to use means such as painting, impregnating, dropping and kneading. The held amount is not particularly limited and can be optionally determined. In case of impregnating the acaricides into substrates, the amount by which substrates are saturated is preferable.

One of the preferable examples of the mite proof materials of the present invention is one in the form of carpet. It can be obtained as follows: one procedure is to spray-coat the acaricides of the present invention in the form of solution on the right side and (or) the other side of usual carpets which are made of pile, base cloth, backing agent and lining cloth, another is, before making the above carpets, to knead the acaricides of the present invention into one or some of pile, base cloth and lining cloth and then make a carpet, and the other is to mix the acaricides of the present invention with a backing agent and make a carpet using the agent according to pre-coating method or jute-lining method.

The pre-coating method mentioned above is to paint the backing agent on base cloth in order to fix the pile and afterward paint again the backing agent there in order to adhere lining cloth on it. The jute-lining method is to paint the backing agent on base cloth interwoven with pile and afterward adhere lining base on it. It is usually preferable for the mite proof carpets made by the methods memtioned above to support about 0.5 to 200 g of the compositions having active ingredients per 1 $m^2$ of the carpets.

As mentioned above, the acaricides of the present invention provide a superior effect when directly applied to tatami, carpet, floor, corridor, mattress, sofa, bedding such as futon or pillow, closet, furniture, storehouse and the like by means of setting, dusting, spraying, painting, aerosolizing and heat vaporization or set mite proof materials which support the acaricides in substrates in the above-mentioned places.

The present invention is more specifically described and explained by means of the following Examples.

EXAMPLE 1

[Effect on Dermatophagoides farinae]

An acetone solution of a test sample was impregnated into a black fine paper (5×5 cm) so as to contain the predetermined amount of active ingredients.

After removing the solvent, this paper was put into a polyethylene bag (6×6 cm) with about three hundred of mites and then the four sides of it were closed. 48 hours later, the number of living mites was counted under a stereomicroscope. Mortality was calculated by means of Abott revision method shown in the formula below. The results are shown on Table 1.

$$\text{adjusted mortality (\%)} = \frac{X - Y}{X} \times 100$$

X: percentage of living mites in untreated group
Y: percentage of living mites in treated group.

TABLE 1

| Experiment No. | Name of test samples (mixed ratio by weight) | Mortality (%) Amount of active ingredient (0.5 g/m$^2$) | Amount of active ingredient (0.1 g/m$^2$) |
| --- | --- | --- | --- |
| 1 | NFC | 100 | 100 |
| 2 | NBA | 100 | 53 |
| 3 | PCMX | 97 | 43 |
| 4 | BCA | 100 | 49 |
| 5 | NFC/NBA(1/1) | 100 | 100 |
| 6 | NFC/PCMX(1/1) | 100 | 95 |
| 7 | NFC/BCA(1/1) | 100 | 92 |
| 8 | NFC/NBA/PCMX(1/1/1) | 100 | 100 |
| 9 | NFC/NBA/BCA(1/1/1) | 100 | 100 |
| 10 | NBA/PCMX/BCA(1/1/1) | 100 | 51 |
| 11 | NFC/NBA/PCMX/BCA(1/1/1/1) | 100 | 92 |
| 12 | PS | 100 | 63 |
| 13 | PB | 100 | 56 |
| 14 | DA | 100 | 47 |
| 15 | MNK | 100 | 42 |
| 16 | CM | 100 | 41 |
| 17 | PS/PB(1/1) | 100 | 65 |
| 18 | PS/DA(1/1) | 100 | 57 |
| 19 | DA/MNK(1/1) | 100 | 42 |
| 20 | MNK/CM(1/1) | 100 | 42 |
| 21 | PS/PB/DA(1/1/1) | 100 | 54 |
| 22 | PS/PB/MNK(1/1/1) | 100 | 57 |
| 23 | PS/DA/MNK(1/1/1) | 100 | 50 |
| 24 | PS/MNK/CM(1/1/1) | 100 | 43 |
| 25 | PS/PB/DA/MNK(1/1/1/1) | 100 | 53 |
| 26 | PS/PB/DA/CM(1/1/1/1) | 100 | 50 |
| 27 | PS/PB/DA/MNK/CM(1/1/1/1/1) | 100 | 48 |
| 28 | PB | 100 | 45 |
| 29 | CBP | 100 | 40 |
| 30 | TFS | 100 | 64 |
| 31 | BIC | 60 | 41 |
| 32 | OPP/SPP(1/1) | 100 | 68 |
| 33 | CIO/MIO(1/1) | 100 | 42 |
| 34 | CBP/TFS(1/1) | 100 | 61 |
| 35 | CBP/BIC(1/1) | 100 | 40 |
| 36 | CBP/SPP(1/1) | 100 | 63 |
| 37 | CBP/CIP/MIO(1/1/1) | 100 | 42 |
| 38 | CBP/TFS/BIC(1/1/1) | 100 | 53 |
| 39 | TFS/OPP/SPP(1/1/1) | 100 | 65 |
| 40 | TFS/CIO/MIO(1/1/1) | 100 | 57 |
| 41 | BIC/OPP/SPP(1/1/1) | 100 | 59 |
| 42 | BIC/CIO/MIO(1/1/1) | 100 | 41 |
| 43 | CBP/TFS/OPP/SPP(1/1/1/1) | 100 | 57 |
| 44 | CBP/TFS/CIO/MIO(1/1/1/1) | 100 | 45 |
| 45 | CBP/BIC/OPP/SPP(1/1/1/1) | 100 | 53 |
| 46 | CBP/BIC/CIO/MIO(1/1/1/1) | 100 | 42 |
| 47 | CBP/TFS/BIC/OPP/SPP(1/1/1/1/1) | 100 | 52 |
| 48 | CBP/TFS/BIC/CIO/MIO(1/1/1/1/1) | 100 | 40 |
| 49 | CBP/TFS/BIC/OPP/SPP/CIO/MIO(1/1/1/1/1/1/1) | 100 | 48 |
| Reference example | dl,d-T80-resmethrin | 51 | 38 |

While it had been known that dl,d-T80-resmethrin was effective on Dermatophagoides farinae, the acaricides of the present invention had an equivalent effect to or a more effect than dl,d-T80-resmethrin.

EXAMPLE 2

[Effect on Tyrophagus putrescentiae]

24 hours after the treatment of Tyrophagus putrescentiae according to the same procedure as Example 1, the number of living mites was counted. Mortality (%) was calculated by means of Abott revision method as in Example 1. The results are shown on Table 2.

TABLE 2

| Experiment No. | Name of test samples (mixed ratio by weight) | Mortality (%) Amount of active ingredient (0.5 g/m$^2$) | Amount of active ingredient (0.1 g/m$^2$) |
| --- | --- | --- | --- |
| 50 | NFC | 100 | 98 |
| 51 | NBA | 100 | 42 |
| 52 | PCMX | 100 | 30 |
| 53 | BCA | 96 | 26 |
| 54 | NFC/NBA(1/1) | 100 | 66 |
| 55 | NFC/PCMX(1/1) | 100 | 63 |
| 56 | NFC/BCA(1/1) | 100 | 63 |

TABLE 2-continued

| Experiment No. | Name of test samples (mixed ratio by weight) | Mortality (%) Amount of active ingredient (0.5 g/m$^2$) | Amount of active ingredient (0.1 g/m$^2$) |
|---|---|---|---|
| 57 | NFC/NBA/PCMX(1/1/1) | 100 | 54 |
| 58 | NFC/NBA/BCA(1/1/1) | 100 | 55 |
| 59 | NBA/PCMX/BCA(1/1/1) | 100 | 39 |
| 60 | NFC/NBA/PCMX/BCA(1/1/1/1) | 100 | 34 |
| 61 | PS | 100 | 48 |
| 62 | PB | 100 | 55 |
| 63 | DA | 100 | 52 |
| 64 | MNK | 100 | 43 |
| 65 | CM | 100 | 45 |
| 66 | PS/DB(1/1) | 100 | 54 |
| 67 | PS/DA(1/1) | 100 | 54 |
| 68 | DA/MNK(1/1) | 100* | 47 |
| 69 | MNK/CM(1/1) | 100 | 40 |
| 70 | PS/PB/DA(1/1/1) | 100 | 52 |
| 71 | PS/PB/MNK(1/1/1) | 100 | 49 |
| 72 | PS/DA/MNK(1/1/1) | 100 | 46 |
| 73 | PS/MNK/CM(1/1/1) | 100 | 45 |
| 74 | PS/PB/DA/MNK(1/1/1/1) | 100 | 53 |
| 75 | PS/PB/DA/CM(1/1/1/1) | 100 | 51 |
| 76 | PS/PB/DA/MNK/CM(1/1/1/1/1) | 100 | 51 |
| 77 | PB' | 100 | 40 |
| 78 | CBP | 100 | 13 |
| 79 | TFS | 42 | 10 |
| 80 | BIC | 95 | 94 |
| 81 | OPP/SPP(1/1) | 100 | 100 |
| 82 | CIO/MIO(1/1) | 100 | 44 |
| 83 | CBP/TFS(1/1) | 100 | 10 |
| 84 | CBP/BIC(1/1) | 100 | 66 |
| 85 | CBP/SPP(1/1) | 100 | 85 |
| 86 | CBP/CIP/MIO(1/1/1) | 100 | 18 |
| 87 | CBP/TFS/BIC(1/1/1) | 100 | 27 |
| 88 | TFS/OPP/SPP(1/1/1) | 100 | 79 |
| 89 | TFS/CIO/MIO(1/1/1) | 98 | 23 |
| 90 | BIC/OPP/SPP(1/1/1) | 100 | 100 |
| 91 | BIC/CIO/MIO(1/1/1) | 100 | 72 |
| 92 | CBP/TFS/OPP/SPP(1/1/1/1) | 100 | 54 |
| 93 | CBP/TFS/CIO/MIO(1/1/1/1) | 100 | 21 |
| 94 | CBP/BIC/OPP/SPP(1/1/1/1) | 100 | 81 |
| 95 | CBP/BIC/CIO/MIO(1/1/1/1) | 100 | 73 |
| 96 | CBP/TFS/BIC/OPP/SPP(1/1/1/1/1) | 100 | 68 |
| 97 | CBP/TFS/BIC/CIO/MIO(1/1/1/1/1) | 100 | 37 |
| 98 | CBP/TFS/BIC/OPP/SPP/CIO/MIO(1/1/1/1/1/1/1) | 100 | 44 |
| Reference example | dl,d-T80-resmethrin | 38 | 5 |

The acaricides of the present invention had an equivalent effect to or a more effect than dl,d-T80-resmethrin on Tyrophagus putressentiae.

EXAMPLE 3

According to the conditions shown on Table 3 following, mite proof materials in the form of carpets were made aiming to make carpets mite-proof.

TABLE 3

| Experiment No. | Pile Material | Pile Kneaded amount of test samples (g/m$^2$) | Base cloth Material | Base cloth Kneaded amount of test samples (g/m$^2$) | Backing agent Material | Backing agent Mixed amount of test samples (g/m$^2$) | Lining cloth Material | Lining cloth Kneaded amount of test sample (g/m$^2$) |
|---|---|---|---|---|---|---|---|---|
| 99 | Polypropylene | — | Polypropylene | — | SBR group | CBP(30) | Jute | — |
| 100 | Polypropylene | — | Polypropylene | — | SBR group | TFS(40) | Jute | OPP(1) SPP(1) (Surface spray) |
| 101 | Polypropylene | — | Polypropylene | BIC(15) | SBR group | CBP(10) | Jute | — |
| 102 | Polypropylene | BIC(10) | Polypropylene | — | EVA group | OPP(1) SPP(5) | Polypropylene Rayon | — |
| 103 | Polypropylene | TFS(15) | Polypropylene | — | EVA group pre-coat | TFS(10) | Polypropylene Rayon | — |
| 104 | Polypropylene | TFS(15) | Polypropylene | — | EVC group | CIO(5) MIO(5) | Polypropylene Rayon | — |
| 105 | Acryl | CBP(3) (Surface | Polypropylene | — | SBR group | CBP(10) | Polypropylene | — |

TABLE 3-continued

| Experiment No. | Pile Material | Pile Kneaded amount of test samples (g/m²) | Base cloth Material | Base cloth Kneaded amount of test samples (g/m²) | Backing agent Material | Backing agent Mixed amount of test samples (g/m²) | Lining cloth Material | Lining cloth Kneaded amount of test sample (g/m²) |
|---|---|---|---|---|---|---|---|---|
| 106 | Acryl | spray) — | Polypropylene | — | EVA group | OPP(20) SPP(20) | Rayon Polypropylene Rayon | — |
| 107 | Nylon | CIO(5) NIO(4) | Rayon | — | SBR group | MIO(10) CIO(10) | Polypropylene Rayon | — |
| 108 | Nylon | — | Rayon | — | SBR group | TFS(15) | Polypropylene Rayon | BIO(5) (Surface spray) |
| 109 | Nylon | — | Rayon | TFS(10) | SBR group | CBP(20) | Polypropylene Rayon | — |
| 110 | Nylon | — | Rayon | — | EVA group pre-coat | TFS(20) Benzylbenzoate | Polypropylene Rayon | — |
| 111 | Polyester | TFS(5) | Polypropylene | — | SBR group | BIC(30) | Polypropylene Rayon | — |
| 112 | Polyester | CBP(3) (Surface spray) | Polypropylene | — | SBR group | OPP(10) SPP(10) | Polypropylene Rayon | — |
| 113 | Polypropylene | — | Polypropylene | — | SBR group | PS(50) | Jute | — |
| 114 | Polypropylene | — | Polypropylene | MNK(10) | SBR group | PB(50) | Jute | — |
| 115 | Polypropylene | — | Polypropylene | — | SBR group | PS(50) | Jute | DA(5) (Surface spray) |
| 116 | Polypropylene | PS(10) | Polypropylene | — | EVA group | DA(40) | Polypropylene Rayon | — |
| 117 | Polypropylene | PB(5) | Polypropylene | — | EVC group | MNK(40) CM(5) | Polypropylene Rayon | — |
| 118 | Acryl | PB(5) | Polypropylene | — | SBR group | PS(30) | Polypropylene Rayon | CM(5) (Surface spray) |
| 119 | Nylon | — | Rayon | — | SBR group | PS(20) Benzylbenzoate | Polypropylene Rayon | — |
| 120 | Nylon | — | Rayon | PS(10) | EVA group | PB(40) | Polypropylene Rayon | PS(1) Diethyltoluamide(3) (Surface spray) |
| 121 | Nylon | PS(2) Diethyltoluamide(5) (Surface spray) | Rayon | — | EVC group | PS(50) | Polypropylene Rayon | — |
| 122 | Polyester | — | Polypropylene | PS(5) | SBr group | PS(50) | Polypropylene Rayon | — |
| 123 | Polypropylene | — | Polypropylene | — | SBR group | NBA(40) | Jute | — |
| 124 | Polypropylene | — | Polypropylene | — | SBR group | PCMX(30) | Jute | NFC(2) (Surface spray) |
| 125 | Polypropylene | NFC(5) | Polypropylene | — | EVA group | BCA(30) | Polypropylene Rayon | — |
| 126 | Acryl | — | Polypropylene | NFC(5) | EVA group pre-coat | BCA(30) | Polypropylene Rayon | — |
| 127 | Nylon | NFC(5) | Rayon | — | SBR group | NFC(3) Benzylbenzoate (30) | Polypropylene Rayon | — |
| 128 | Nylon | NFC(1) Benzylbenzoate (Surface spray) | Rayon | — | SBR group | NBA(30) | Polypropylene Rayon | — |
| 129 | Polyester | NBA(5) (Surface | Polypropylene | NFC(5) | EVC group | POMX(20) | Polypropylene | NFC(2) (surface |

TABLE 3-continued

| Experiment No. | Pile Material | Pile Kneaded amount of test samples (g/m²) | Base cloth Material | Base cloth Kneaded amount of test samples (g/m²) | Backing agent Material | Backing agent Mixed amount of test samples (g/m²) | Lining cloth Material | Lining cloth Kneaded amount of test sample (g/m²) |
|---|---|---|---|---|---|---|---|---|
| 130 | Polypropylene | — (spray) | Polypropylene | PB(5) | SBR group | PB'(40) | Rayon Jute | spray) — |
| 131 | Polypropylene | PB'(10) | Polypropylene | — | EVA group | PB'(30) | Jute | — |
| 132 | Polypropylene | — | Polypropylene | — | EVC group | PB'(50) | Jute | — |
| 133 | Acryl | PB'(2) (Surface spray) | Polypropylene | — | EVC group | PB'(25) DEET(10) | Jute | — |
| 134 | Nylon | PB'(3) | Rayon | — | EVC group pre-coat | PB'(20) | Polypropylene Rayon | — |
| 135 | Nylon | — | Rayon | — | SBR group | PB'(40) | Polypropylene Rayon | — |
| 136 | Polyester | AA(3) (Surface spray) | Polypropylene | — | SBR group | PB'(25) | Polypropylene Rayon | PB'(5) (Surface spray) |

The following test was carried out with respect to each of the mite proof carpets made according to the above-mentioned conditions.

(Testing method)

A medium containing about ten thousand of mites of Dermatophagoides farinae was set in the center of both the each of tested carpets and an untreated carpet (20×20 cm each) and put each of them at the bottom of a container (41×31×22 cm). After allowing it to stand for two days under the condition of 25° C. and 64% RH, the mites on the right side or the other side of each carpet were sucked by a vacuum cleaner with putting two sheets of 200 mesh of nylon gauze at the conector of the suction tube. After removing the nyron gauze from the vacuum cleaner the mites were brushed into a 300 ml beaker which contains 100 ml of Darling's solution. After stirring, the solution was poured into a centrifugal tube and centrifuged at the rate of 1000 rpm. The supernatant was poured into a Buchnr funnel with a filter on it and filtered by means of suction filtration. The number of living mites on the filter was counted and the result of mortarity was calculated according to the following formula.

$$\text{adjusted mortality (\%)} = \frac{X - Y}{X} \times 100$$

X: percentage of living mites in untreated carpet group
Y: percentage of living mites in acaricide treated carpet group The above test was repeated three times and the average of mortalities was calculated. As a result, the mortality was 100% in all cases.

EXAMPLE 4

A trace quantity of perfume and 20 ml of ethyl cellosolve were added to each of 15 g of test samples shown on Table 4. Further, odorless kerosene was added to it so as to make the total volume 150 ml. Then, a pressure can for aerosol (capacity: 400 ml) was filled with both the above solution and 150 ml of the mixture of the liquefied petroleum gas and dimethyl ether (ratio by volume 1:1), put onto a jet equipment and sealed up.

The acaricides in the form of aerosol of the present invention were obtained.

By using each aerosol obtained in the above, the effect of prevention of mites was tested by the same procedure as in Example 1.

(Testing method)

Each aerosol was sprayed for 3 seconds onto a fine paper (30×30 cm) as equal as possible. After allowing it to stand for one day under ordinary temprature, it was cut into 5×5 cm sheets and then the effect of prevention of mites was tested by the same procedure as in Example 1.

The above test was repeated three times. The results are shown on Table 4 according to the average of the mortalities.

TABLE 4

| Experiment No. | Names of test samples (mixed ratio by weight) | Mortality (%) |
|---|---|---|
| 137 | NFC | 100 |
| 138 | NBA | 100 |
| 139 | NFC/NBA(1/1) | 100 |
| 140 | NFC/PCMX(1/1) | 100 |
| 141 | NFC/BCA(1/1) | 100 |
| 142 | NBA/PCMX(1/1) | 100 |
| 143 | NBA/BCA(1/1) | 100 |
| 144 | PS | 100 |
| 155 | PB | 100 |
| 156 | DA | 100 |
| 157 | PS/PB(1/1) | 100 |
| 158 | PS/DA(1/1) | 100 |
| 159 | MNK/CM(2/1) | 100 |
| 160 | PS/dl,d-T80-resmethrin(4/1) | 100 |
| 161 | PS/benzylbenzoate(1/1) | 100 |
| 162 | BS | 100 |
| 163 | PB | 100 |
| 164 | PB/BS(1/1) | 100 |
| 165 | PB/AC(1/1) | 100 |
| 166 | BS/AB(4/1) | 100 |
| 167 | CBP | 100 |
| 168 | TFS | 100 |
| 169 | BIC | 100 |
| 170 | OPP/SPP(1/1) | 100 |
| 171 | CIO/MIO(1/1) | 100 |
| 172 | CBP/TFS(1/1) | 100 |
| 173 | CBP/BIC(1/1) | 100 |
| 174 | CBP/dl,d-T80-resmethrin(2/1) | 100 |

As shown on Table 4, each aerosol has an enough effect on prevention of mites.

EXAMPLE 5

A each test sample on Table 5 was mixed with each solvent shown on the same Table, a non-woven fablic (made of polyethyene-pulp of 300 μm thick and 1 m² area) was impregnated with the above solvent so as to contain 1 g of each of test samples in amount and dried, and thus the mite proof materials in the form of sheet of the present invention were obtained.

This sheet was cut into 5×5 cm sheets and then effect of prevention of mites was tested by the same procedure as in Example 1.

TABLE 5

| Experiment No. | Test samples (concentration %) | Names of solvent (mixed ratio by weight) |
| --- | --- | --- |
| 175 | NFC (2) | n-Hexane |
| 176 | NBA (3) | n-Hexane |
| 177 | PCMX (3) | Solventnaphtha |
| 178 | BCA (3) | Solventnaphtha |
| 179 | NFC (1) PCMX (2) | Solventnaphtha |
| 180 | PCMX (6) | Polyvinylchloride ink (14) Toluene (80) |
| 181 | PS (3) | n-Hexane |
| 182 | PB (3) | n-Hexane |
| 183 | DA (3) | n-Hexane |
| 184 | PS (2) PB (1) | n-Hexane |
| 185 | PS (2) DA (1) | n-Hexane |
| 186 | PS (3) MNK (3) | Polyvinylchloride ink (14) Toluene (80) |
| 187 | MNK (2) CM (1) | Solventnaphtha |
| 188 | CBP (3) | n-Hexane |
| 189 | TFS (3) | n-Hexane |
| 190 | OPP (1) SPP (1) | n-Hexane |
| 191 | CIO (1) MIO (1) | n-Hexane |
| 192 | BIC (1) | Dimethylsulfoxide |
| 193 | CBP (1) | Polyvinylchloride ink (19) Toluene (80) |
| 194 | CBP (1) TFS (1) | Solventnaphtha |
| 195 | OPP (5) SPP (5) | Water |
| 196 | CIO (1) MIO (1) | water |
| 197 | BS (3) | n-Hexane |

TABLE 5-continued

| Experiment No. | Test samples (concentration %) | Names of solvent (mixed ratio by weight) |
| --- | --- | --- |
| 198 | PB (3) | n-Hexane |
| 199 | BS (6) | Polyvinylchloride ink (14) Toluene (80) |
| 200 | BS (2) PB (1) | Solventnaphtha |

As a result, all samples showed almost 100% of mortality and thus enough effects of prevention of mites.

EXAMPLE 6

Each of the test samples employed in Example 5 was stirred and mixed well with the same weight of oxidized silicon and powdered. Then the acaricides of the present invention in the form of powder were obtained. The effect of prevention of mites of the above powder was tested by the following method.

(Testing Method)

After 2 cm-cut-straws were heated to exterminate insect, 5 g of them was put into a 100 ml trigonal flask, and then 0.05 g of each powder was put in it. Then it was mixed well and allowed to stand for one day under the condition of 25° C. and from 85 to 90% RH. Afterward, about four hundred of mites of Tyrophagus putrescentiae were put into this flask and then it was allowed to stand for two more days under the same condition as above and living mites were removed by means of heat-flushing out method.

The number of living mites was counted and mortality was calculated according to the formula in Example 3.

As a result, each powder showed almost 100% of mortality and thus enough effect of prevention of mites.

We claim:

1. A method for killing mites on a material which comprises applying to said mites a composition containing a miticidal amount of phenyl salicylate or of benzyl salicylate.

2. A method according to claim 1, wherein the material is in a house.

3. A method according to claim 2, wherein the material is a tatami mat or a carpet.

4. A method according to claim 2, wherein the material is bedding or furniture.

* * * * *